(12) United States Patent
Jourdain et al.

(10) Patent No.: US 6,344,647 B1
(45) Date of Patent: Feb. 5, 2002

(54) MINIATURIZED PHOTOACOUSTIC SPECTROMETER

(75) Inventors: Anne Jourdain, Cologne; Claude Bieth, Claix; Hubert Bono, Haute Jarrie; Olivier Constantin, Grenoble, all of (FR)

(73) Assignee: Commissariat a l' Energie Atomique, Paris (FR)

( * ) Notice: Subject to any disclaimer, the term of this patent is extended or adjusted under 35 U.S.C. 154(b) by 0 days.

(21) Appl. No.: 09/297,087

(22) PCT Filed: Sep. 18, 1998

(86) PCT No.: PCT/FR98/02003

§ 371 Date: May 17, 1999

§ 102(e) Date: May 17, 1999

(87) PCT Pub. No.: WO99/15879

PCT Pub. Date: Apr. 1, 1999

(30) Foreign Application Priority Data

Sep. 19, 1997 (FR) .............................. 97 11697

(51) Int. Cl.$^7$ .............................................. G01N 21/17
(52) U.S. Cl. .......................... 250/339.07; 250/339.08; 250/343
(58) Field of Search ........................... 250/339.07, 343, 250/339.08

(56) References Cited

U.S. PATENT DOCUMENTS 4,740,086 A * 4/1988 Oehler et al. ................ 356/432
4,818,882 A    4/1989 Nexo et al.

FOREIGN PATENT DOCUMENTS

| EP | 0668 490 | 8/1995 | |
|----|----------|--------|---|
| EP | 0689229 | 12/1995 | |
| EP | 0709659 A2 * | 1/1996 | ............. G01J/3/26 |
| EP | 0709659 | 5/1996 | |

* cited by examiner

Primary Examiner—Constantine Hannaher
Assistant Examiner—Otilia Gabor
(74) Attorney, Agent, or Firm—Oblon, Spivak, McClelland, Maier & Neustadt, P.C.

(57) ABSTRACT

A miniaturized photoacoustic spectrometer made from a series of stacked substrates. An infrared source is formed in a first substrate. A filter is formed in a second substrate. A micro-trough is machined in a third substrate and a microphone is formed in a fourth substrate. A fifth substrate has a metallic deposit for reflecting light emitted by the infrared source. Resin sealing is provided between the substrates.

42 Claims, 8 Drawing Sheets

MINIATURIZED PHOTOACOUSTIC SPECTROMETER

BACKGROUND OF THE INVENTION

1. Field of the Invention

The present invention relates to a photoacoustic spectrometry device, used for example for analysing gases. It more particularly relates to a miniaturized photoacoustic spectrometer. This device is implemented from stacks of elementary components, capable of being implemented by substrate etching, metallic deposition and substrate assembly techniques, of the type used in microelectronics.

2. Discussion of the Background

The principle of photoacoustic spectroscopy for analysing gases has been discussed in the article by J. Christensen entitled "The Brüel Kjaer Photoacoustic Transducer System and its Physical Properties". The device described in this document has:

an infrared hot source, a mechanical "chopper", which modulates the intensity of the source, an interferential optical filter, a cylindrical trough, two matched microphones, the sum of the signals originating from these microphones making it possible to double the photoacoustic signal and nullify the noise due to external vibrations.

In this device, the source is at a distance from the trough in order to avoid any heating of the gas. To that end, the use of an ellipsoidal mirror coupled to the source makes it possible to achieve suitable collimation of the light beam.

The document WO-96/24831 describes a photoacoustic detector having a chamber for receiving a gas to be measured, an infrared light beam capable of passing through this chamber, and a pressure sensor capable of measuring the pressure variations in the chamber, which are induced by an infrared beam. The chamber is formed by the assembly of two semiconductor elements, for example silicon or quartz elements, implemented in planar technology. The pressure variations are detected by means of a membrane.

Implementation of a photoacoustic spectrometer, of miniature size, allowing integration of all the elements (radiation source, filter, trough, microphone) in a compact manner, is not known.

SUMMARY OF THE INVENTION

An object of the invention is a photoacoustic spectrometer having an infrared source which can be modulated electrically, an interferential optical filter, a microphone and a micro-trough, each of these elements being integrated on a semiconductor substrate or on at least one, or with the help of at least one semiconductor substrate, for example made of silicon.

An object of the invention is therefore a photoacoustic microspectrometer, obtained by assembly or sealing of four elements integrated on a semiconductor: an infrared source which can be modulated electrically, an interferential optical filter, a micro-trough, and a microphone.

Each of the elements composing the spectrometer according to the invention can be integrated on, or implemented with the help of, one or two semiconductor substrates.

According to a first particular embodiment, an object of the invention is a photoacoustic spectrometer having:

an infrared source implemented in a first semiconductor substrate, a filter implemented with the help of a second semiconductor substrate, a micro-trough formed in a third semiconductor substrate, a microphone implemented with the help of the third semiconductor substrate and a fourth semiconductor substrate.

According to a second particular embodiment, an object of the invention is a photoacoustic spectrometer, having:

an infrared source implemented in a first semiconductor substrate, a Fabry-Pérot interferential filter formed with the help of a second and a third semiconductor substrates, a micro-trough Implemented partially in the third semiconductor substrate and partially in a fourth semiconductor substrate, a microphone implemented with the help of the fourth and a fifth semiconductor substrates.

According to a third particular embodiment, an object of the invention is a photoacoustic spectrometer, having:

an infrared source, implemented in a first semiconductor substrate, a Fabry-Pérot interferential filter formed with the help of the first and a second semiconductor substrates, a micro-trough implemented in the second semiconductor substrate, a microphone implemented on the surface of a third semiconductor substrate.

According to a fourth particular embodiment, an object of the invention is a photoacoustic spectrometer, having:

an infrared source implemented in a first semiconductor substrate, a Fabry-Pérot interferential filter implemented with the help of the first and a second semiconductor substrates, a microphone and a micro-trough, implemented in the second semiconductor substrate.

In the device according to the invention, the mechanical chopping of the beam can be replaced by direct electrical modulation of the injection current in the infrared source.

The source can have a metallic grid, or a metallic filament, supported by a membrane above a cavity etched in a semiconductor substrate. This grid, or this filament, is for example made of silicon nitride, or platinum, or tantalum, or titanium, or tungsten, or molybdenum, or chromium, or nickel, or one of their alloys, or TiN.

Preferably, the source is placed in a cavity. Putting this cavity under vacuum moreover makes it possible to avoid heating problems due to the gaseous medium, which can be critical in a miniature device.

The interferential filter can be a filtering substrate.

This can also be a Fabry-Pérot tunable filter.

It can then have a first, fixed, mirror and a second, movable, mirror, these mirrors delimiting, at rest, a resonant cavity of length d, first and second control electrodes being associated respectively with these first and second mirrors, the application of an electrical voltage between the control electrodes allowing implementation of a displacement of the movable mirror with respect to the fixed mirror, and therefore modifying the length d of the resonant cavity.

According to another embodiment, the Fabry-Pérot tunable filter has:

a first mirror, with which a floating electrode is associated, a second mirror, with which a first and a second control electrode are associated, one out of the first and second mirrors being fixed while the other is movable, a resonant cavity, of length d, delimited by the first and second mirrors, the application of an electrical voltage between the two control electrodes bringing about a displacement of the movable mirror with respect to the fixed mirror and therefore modifying the length d of the resonant cavity.

In this embodiment, the electrode associated with one of the mirrors is a floating electrode, and no contact connection is to be implemented on the side of this mirror. There is therefore, in this system, only a single level of contact to be made, corresponding to the control electrodes. The device is therefore easier to implement, since a contact connection on both levels of mirror is difficult and requires a local stack of highly doped layers.

The fixed and movable mirrors can be implemented by stacking of multilayers at $\lambda/4$, on the surface of semiconductor substrates.

The movable mirror can be implemented by a membrane situated above a cavity implemented in a semiconductor substrate.

The floating electrode and the corresponding mirror can be implemented on the surface of one of the semiconductor substrates.

The control electrodes and the corresponding mirror can be implemented on the surface of another of the semiconductor substrates.

For example, the movable mirror can be composed of a membrane etched in the second semiconductor substrate.

As for the control electrodes, they can be formed on either side of a reflective area of the mirror with which they are associated. In other words, this mirror has a reflective central area, and lateral areas on which the control electrodes are formed.

This reflective central area can have a circular form. This circular form, delimited by the control electrodes, allows, if the corresponding mirror is movable, a perfectly plane displacement of the movable reflective area, since the electrostatic attraction takes place only at the periphery of this area, which makes it possible to have a diaphragmed filter output.

The control electrodes can be implemented in a metallic deposit. Furthermore, electrical contacts can be made directly on the control electrodes, on the surface of the substrate on which they are formed.

Preferably, the control electrodes also form an input diaphragm of the micro-trough.

According to another aspect, one of the walls of the micro-trough is constituted by the microphone membrane.

According to yet another aspect of the invention, the microphone can have a membrane, a first electrode associated with, or formed on, this membrane, and a second electrode, the excess pressures in the micro-trough being detected by variation in the capacitance of the air gap defined by the first and second electrodes.

According to yet another aspect, the microphone has a membrane end a first electrode associated with this membrane, both implemented on a semiconductor substrate, and a second electrode implemented on another semiconductor substrate.

When one of the walls of the micro-trough is constituted by the microphone membrane, the said membrane can be implemented in a coped semiconductor material, the microphone also having a counter electrode. The latter makes it possible to detect the vibrations of the membrane by measuring the variation in the capacitance formed by the membrane of doped semiconductor material and the counter electrode.

The microphone membrane can then be situated on the surface of a substrate, etched under the membrane.

When the tunable filter has a membrane, the latter can be used as both a filter membrane and a microphone membrane. In this case, control of the filter and detection of the pressure variations are carried out with the help of one and the same system. The same electrodes as those which control the filter can then be used to measure the excess pressure created in the micro-trough, that is to say that filter and microphone are as it were combined, and reduced to a single common membrane. In this case, and in order not to create any parasitic photoacoustic signal in the cavity due to absorption of the gas to be measured or of another gas present at the same time, the cavity is preferably placed under a neutral atmosphere, for example under argon. In principle, the excess pressures created in the trough are sufficiently small for the tuning of the filter to the wavelength not to be lost: however, and in order to limit any detuning, means for automatic control position-wise of the membrane can be provided.

BRIEF DESCRIPTION OF THE DRAWINGS

In any case, the characteristics and advantages of the invention will emerge more clearly in the light of the description which follows. This description relates to the example embodiments, given by way of explanation and being non-limitative, referring to accompanying drawings in which.

DETAILED DESCRIPTION OF EMBODIMENTS OF THE INVENTION

Figure 1:
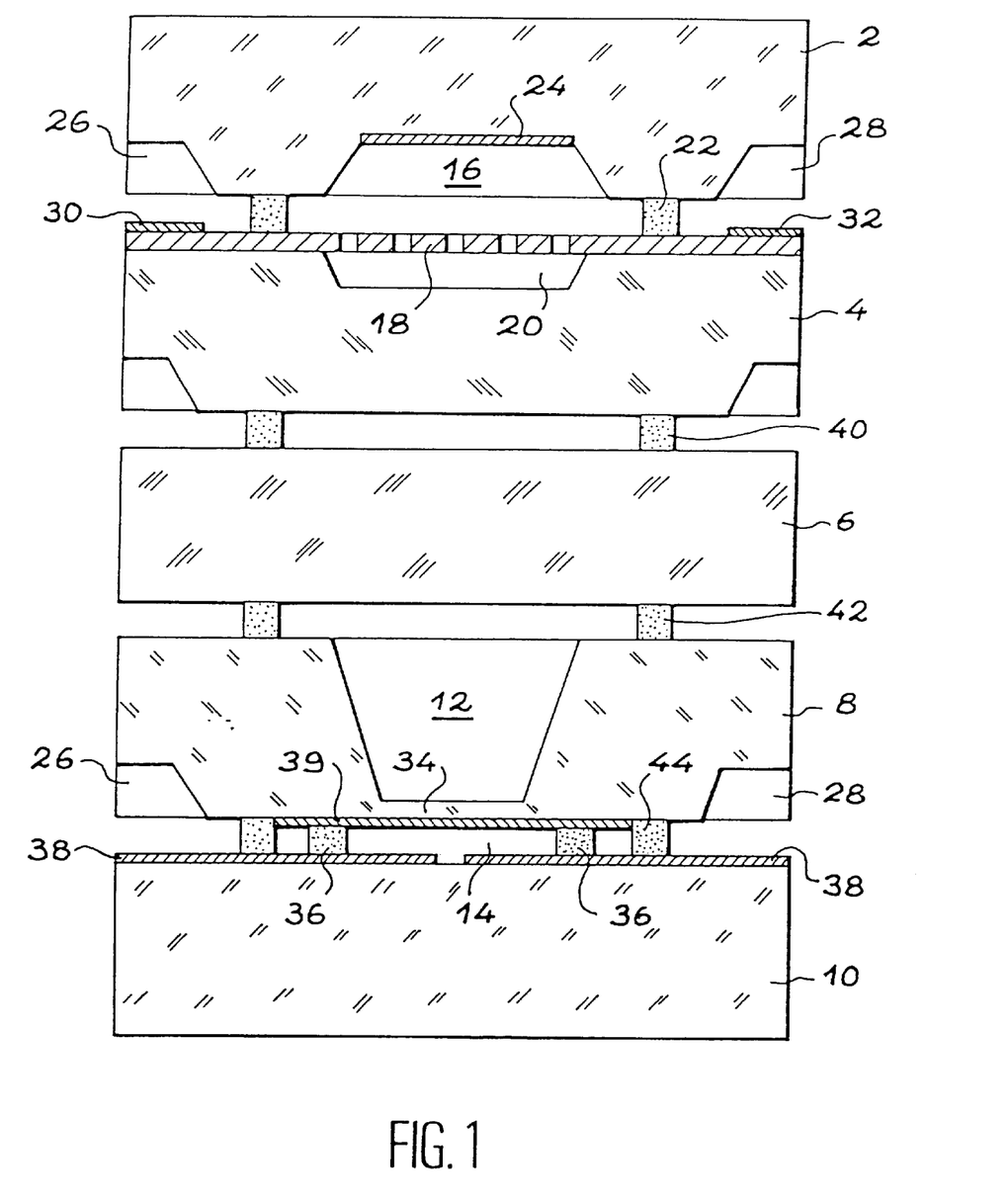
FIG. 1 depicts a first embodiment of a photoacoustic spectrometer according to the invention.

According to a first embodiment, a device according to the invention 1 is composed of an infrared source under vacuum (wafers, or substrates, 2 and 4 of a semiconductor material), a standard optical filter (wafer, or substrate, 6 of a semiconductor material), a micro-trough (wafer, or substrate, 8 of a semiconductor material) 12 and a capacitive microphone 14 (wafers, or substrates, 8 and 10 of a semiconductor material), that is in total five substrates, four of which are machined.

The wafers 2 and 4 (for example made of standard Si) form the infrared source enclosed in a cavity under vacuum 16, 20. This is for example a full sheet TiN layer with small holes made in it, coated with silica, and carried by a silicon nitride membrane 18. The membrane is freed from the front face of the wafer 4 by etching of a sacrificial layer (resin or tungsten (W)), thus leaving a cavity 20 in the substrate. The cover formed by the wafer 2, and in which a cavity 16 is etched, makes it possible to place the source under vacuum when the sealing 22 is carried out. A metallic deposit 24 on the bottom of the cavity 6 forms a reflecting means and makes it possible to recover almost all the light emitted by the source. Two other small cavities 26, 28, at both ends of the cover, facilitate contact connection in the contact connection areas 30, 32 as well as cutting.

The source is for example modulated around 20 Hz.

The sealing 22 is for example resin sealing, under vacuum.

The wafer 6 constitutes the filter. It is inserted into the system when the final sealing is carried out.

The trough 12 is machined in the wafer 8 (this is for example an SOI wafer, with an $SiO_2$ layer of thickness 0.7 $\mu$m, and a doped Si layer, 0.3 $\mu$m thick; standard SOI can also be taken, for example with a 0.4 $\mu$m $SiO_2$ layer and an Si layer, 0.2 $\mu$m thick) at the time of etching a membrane 34 of the microphone. A row of silica pads 36 makes it possible to control the thickness of the air gap 14 between the wafers 8 and 10. Finally, metallic deposits 38, 39 on the two opposite faces constitute two measuring electrodes, a floating electrode being formed by the membrane 39. The sealings 40, 42, 44 can be resin sealings, which provide at least one vent for equalizing the external and internal pressures. The diameter of the vent is calculated to have a low cut-off frequency, typically 1 Hz.

To give an order of magnitude for the different elements, the membrane 18 of the source can have a surface area of 2×2 $mm^2$, the membrane 34 of the microphone having the same size, the trough has a width of around 2 mm and the vent a diameter of around 10 $\mu$m.

Figure 2:
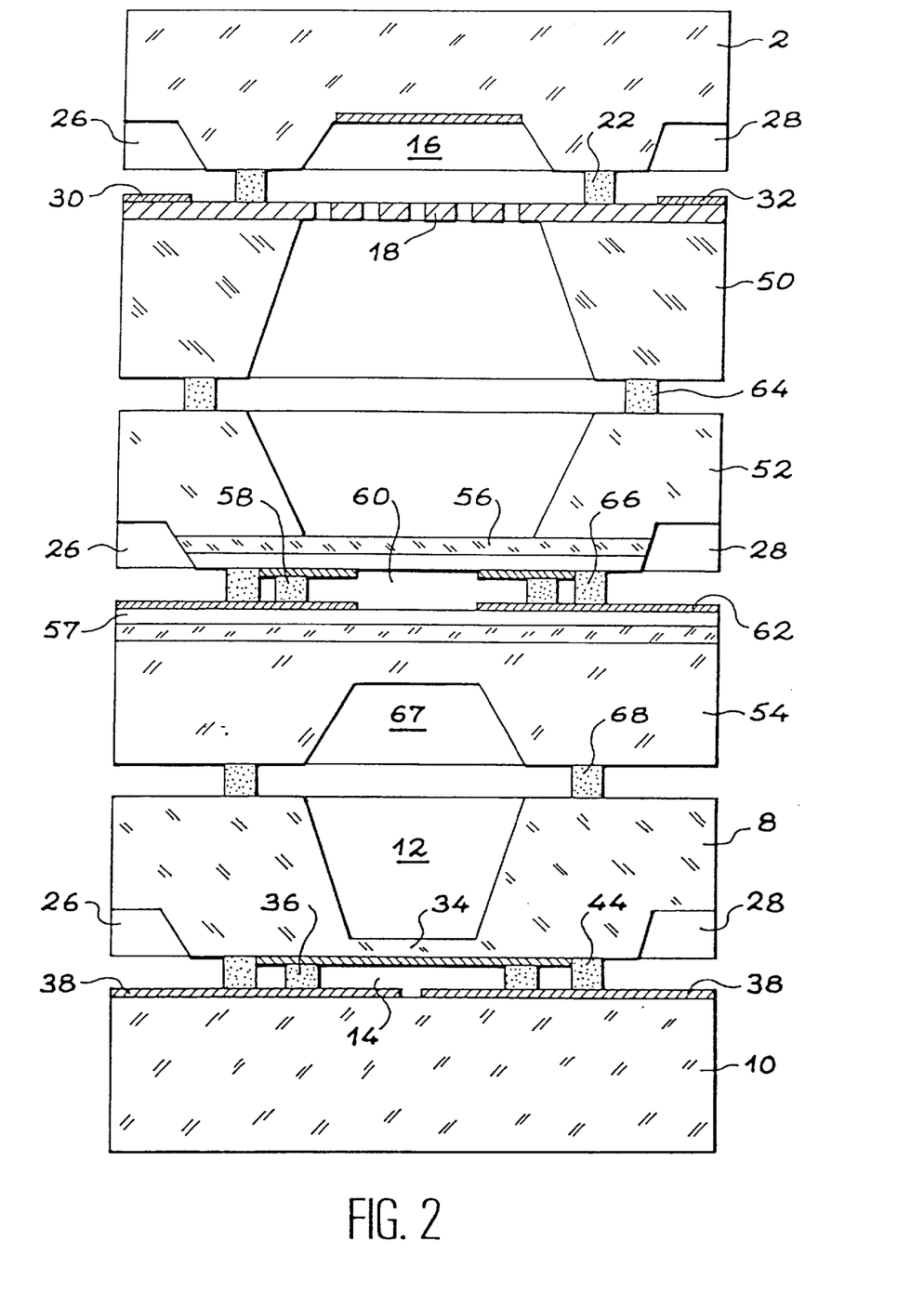
FIG. 2 depicts a second embodiment of a photoacoustic spectrometer according to the invention.

The stack of FIG. 2 repeats that of FIG. 1 while integrating a tunable filter. Numerical references identical to those of FIG. 1 designate identical or corresponding elements therein. The stack is obtained by sealing six semiconductor substrates 2, 8, 10, 50, 52, 54, three of which are vacuum-tight.

The wafers 2 (which serves as a cover) and 50 form the source whose membrane 18 is freed by the rear face of the wafer 50. The wafers 2 and 50 are for example standard silicon substrates.

The wafer 52 is for example an SOI wafer (for example: an $SiO_2$ layer of thickness 0.7 $\mu$m and an Si layer of thickness 0.3 $\mu$m). It is used among other things for the rear face freeing of a membrane 56 of the tunable Fabry-Pérot.

A row of silica pads 58 of thickness $\lambda/2$, $\lambda$ being the working wavelength, makes it possible to control the width of a resonant cavity 60 (the Fabry-Pérot cavity). An annular metallic deposit 62 on the front face of the wafer 54 forms the control electrode of the filter, and also provides a diaphragm function at the input of the micro-trough 67. The membrane 56 of the wafer 52 forms a floating electrode. The faces 56, 57 of the substrates 52, 54 are made reflecting by deposition of dielectric multilayers (at $\lambda/4$). This stack has the advantage of leaving the optical path free between the source and the filter.

The resin sealings 22 and 64 are preferably implemented under atmosphere. The sealing 66 makes it possible to place the source/Fabry-Pérot assembly under vacuum. Placing the filter under vacuum gives a good mechanical behaviour to the membrane 56.

A volume 67 is etched on the rear face of the wafer 54 (which is of SOI type (for example: $SiO_2$ of thickness 0.7 $\mu$m and Si of thickness 0.3 $\mu$m)), for example over one half of the substrate, depth-wise, so that its aperture is identical to that of the diaphragmed output of the filter, in order to minimize the dead volumes.

The microphone 14 is implemented in the wafers 8 and 10: the rear face etching of a volume 12 in the wafer 8 (of SO type (for example: $SiO_2$ of thickness 0.7 $\mu$m and Si of thickness 0.3 $\mu$m)), allows the freeing of a detection membrane 34 of doped silicon, so that the trough has a depth of around a substrate and a half (volume 67+volume 12). A metallic deposit 38 on the front face of he counter-wafer 10 (standard semiconductor or standard substrate) constitutes the counter electrode of the microphone, a floating electrode being formed by the membrane 34. The thickness of the air gap 14 is controlled by the same principle of silica pads 36 as that used for the filter 58.

The resin sealings 68, 44 of the wafers 54, 8 and 10 can provide a vent for equalizing the internal and external pressures.

Lateral cavities 26, 28 in the wafers 2, 52 and 8 make it possible to define the cutting path for freeing the contacts.

Figure 3:
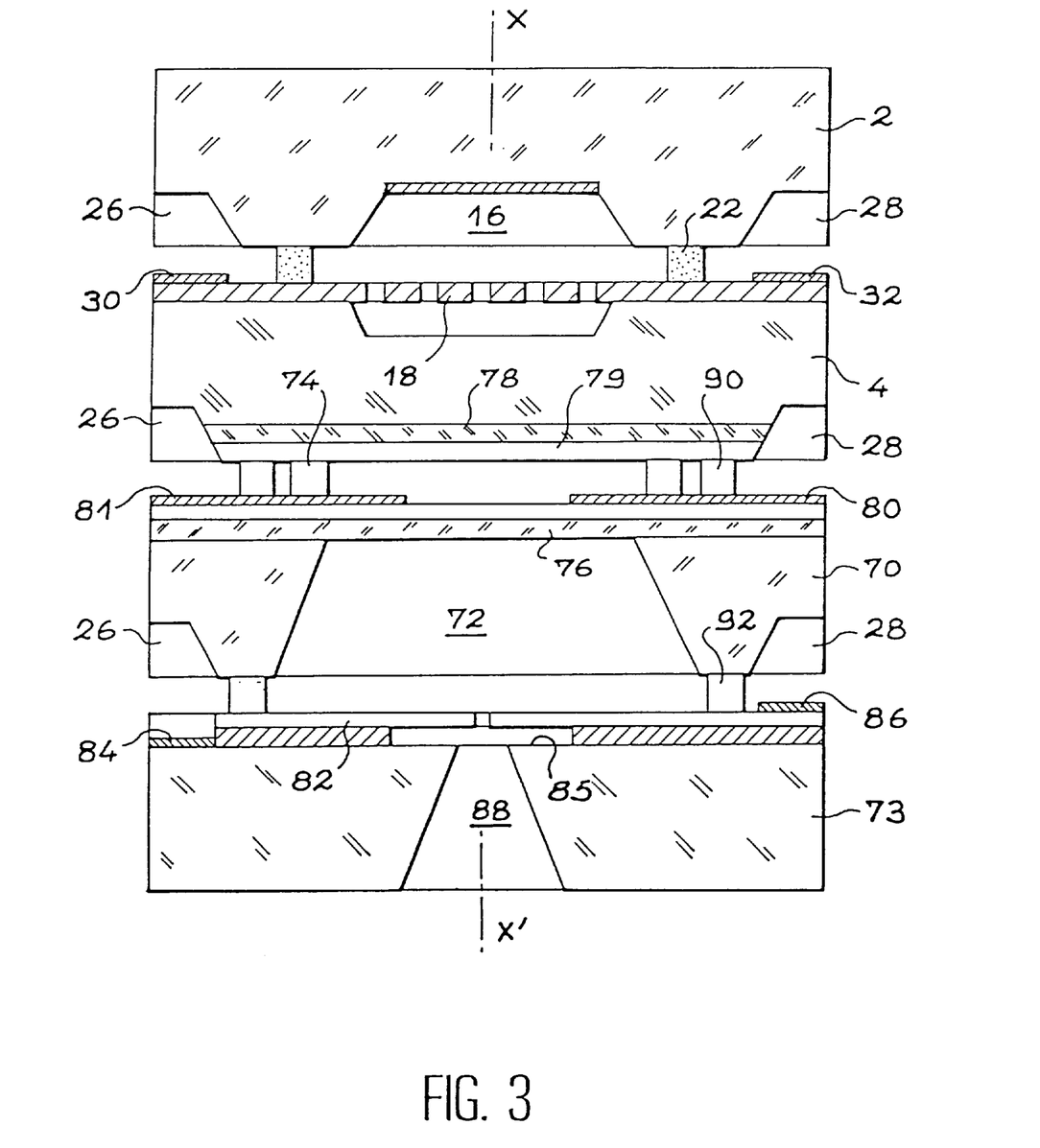
FIG. 3 depicts a third embodiment of a photoacoustic spectrometer according to the invention.

A simplified stack is depicted in FIG. 3. Numerical references identical to those of FIGS. 1 or 2 designate identical or corresponding elements therein. The wafers 2 and 4 form the source under vacuum carried by a silicon nitride membrane 18 freed by the front face of the wafer 4. The sealing 22 is a resin sealing, under vacuum.

The wafers 4 and 70 (of SOI type: for example: $SiO_2$ of thickness 0.7 $\mu$m and Si of thickness 0.3 $\mu$m), simultaneously form the filter and the trough 72. Silica pads 74 define the air cavity between two dielectric mirrors 76 and 78. A metallic deposit 80 on the membrane 76 forms the control electrode and can also provide the diaphragm function. The floating electrode is formed by the doped silicon layer at the surface of the mirror 78. The cavities 26, 28 are etched on the rear face of the wafers 2 and 4 and 70 in order to clear the contacts 30, 32 and 80, 81, 84 and 86 at the time of cutting.

The microphone is implemented in the wafer 72 (of SOI type: for example of standard SOI, with 0.4 $\mu$m of $SiO_2$ and 0.2 $\mu$m of Si; thicker layers can also be used) by front face freeing no a doped silicon membrane 82. The measuring capacitance is formed by the membrane 82 and a counter electrode (the counter electrode is formed by the surface 85 of the substrate 72 cleared after etching of the $SiO_2$ layer) by virtue of contacts 84, 86. The etched rear volume 88 eliminates fluid compression problems at the time of deflection of the membrane.

The resin sealings 90, 92 of the wafers 4 and 70 close the micro-rough on the microphone. A vent for equalizing the internal and external pressures can be provided.

Figure 4:
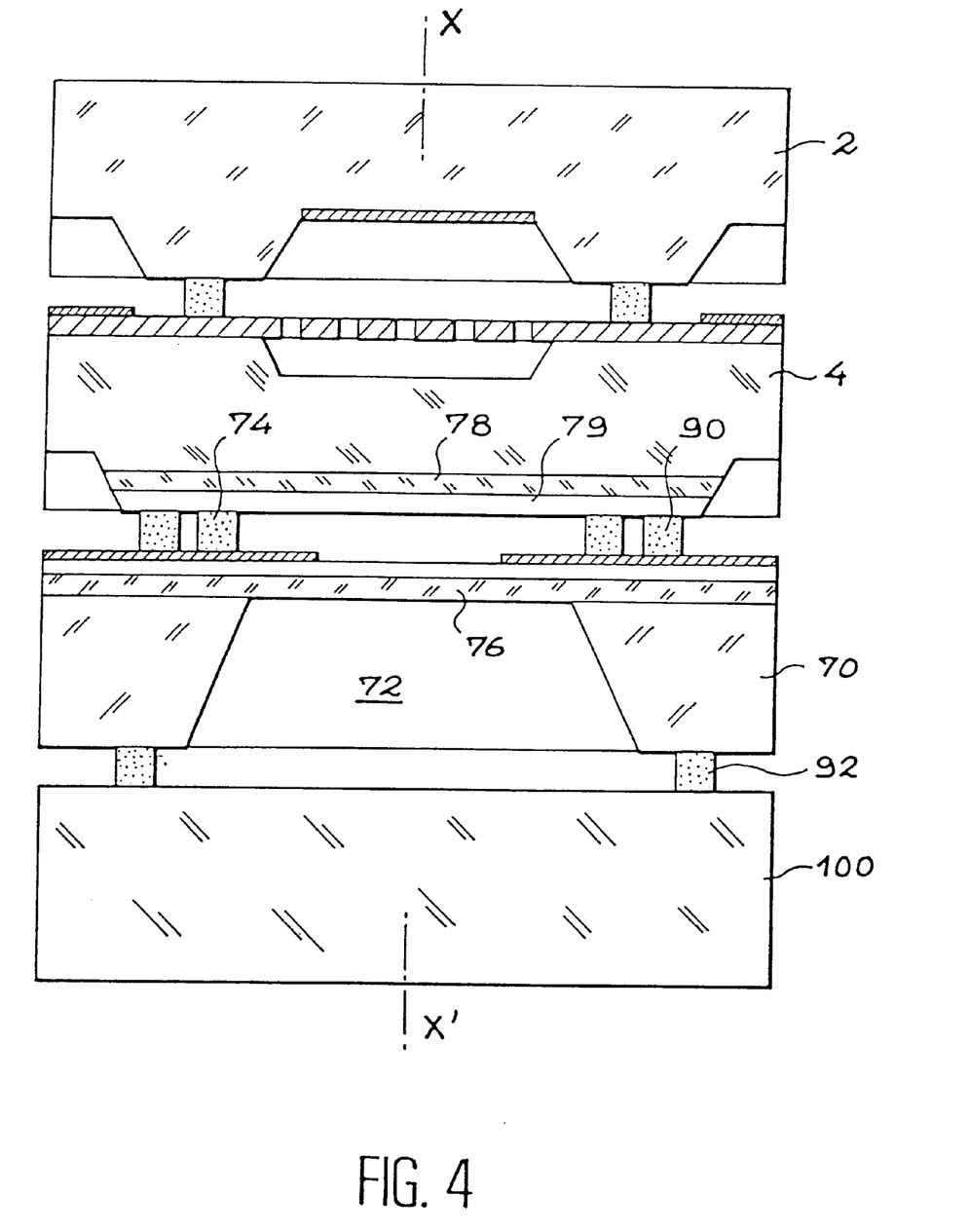
FIG. 4 depicts a fourth embodiment of a photoacoustic spectrometer according to the invention.

Finally, a simpler solution, illustrated in FIG. 4, consists of making the filter and microphone membranes common. This is a stack similar to the previous one (FIG. 3), except for the wafers 4 and 70 (of SOI type: for example $SiO_2$ of thickness 0.7 $\mu$m and Si of thickness 0.3 $\mu$m) which simultaneously form the filter and the microphone with a common membrane 76, and the trough 72. The metallic deposit 80 on the membrane 76 is used as both a control and a measuring electrode as well as, possibly, a diaphragm. The floating electrode is formed by the doped silicon layer at the surface of the mirror 78. The sealing 90 is implemented under a neutral atmosphere (Argon for example).

The last resin sealing 92 of the wafers 70 and 100 closes the micro-trough and can provide a vent for equalizing the internal and external pressures.

In the various embodiments disclosed above, the source has been described by reference to a full sheet TiN layer with holes made in it and coated with silica. Other types of source can be implemented, within the context of a device according to the invention. In particular, the source can be composed of a metallic grid or filament, supported by a membrane, above a cavity etched in a semiconductor substrate. The grid, or the filament, can for example be made of silicon nitride, or platinum, or tantalum, or titanium, or tungsten, or molybdenum, or chromium, or nickel, or one of their alloys.

The source can for example be a miniaturized infrared radiation source as described in the document FR-96 11866 (dated Sep. 30, 1996). Such a source has at least one self-supported microfilament, comprising a metallic material, intended to emit infrared radiation under the action of an electrical current passing through it. The microfilament can have the form of a film of sufficiently small thickness to have a low thermal inertia, compatible with the emission periods of the infrared radiation. The microfilament can be composed of a metallic strip covered with at least one thin layer of a material improving the emissivity of the microfilament in at least part of the infrared spectrum.

The metallic material can be chosen from among the list of materials already given above. The material improving the emissivity of the microfilament is preferably chosen from among the nitrides (for example $Si_3N_4$), silicides (for example SiC, SiMo), oxides (for example $SiO_2$, $Al_2O_3$) or borides.

In every case, the radiation source generates infrared radiation which passes through the interferential filter and reaches the trough, where its absorption takes place. The microphone is disposed so as to detect a pressure variation in the trough.

In the embodiments described above in relation to FIGS. 3 and 4, the filter used is an electrostatically controlled and tunable Fabry-Pérot interferential filter.

This structure has a first, fixed, mirror 78, with which a floating electrode 79 is associated. The latter can be constituted by formation of a doped layer in the substrate 4, forming an integral part of the mirror: this is the external layer of the dielectric mirror. Facing the fixed mirror 79 there is a second mirror 76, movable along the axis XX' of the spectrometer. With this second mirror there are associated two control electrodes designated by the reference 80. The said electrodes are implemented for example by metallization of part of a reflecting membrane forming the second mirror 76.

The two mirrors are kept at a distance d with respect to one another. This distance is in fact the length of the resonant cavity delimited by the mirrors 76, 78.

The two mirrors are kept at a distance d, in FIGS. 3 and 4, with the help of pads 74. This can also be achieved with the help of braces or cross-pieces.

The application of an electrical voltage, with the help of means not depicted in the figures, between the control electrodes 80, brings about a displacement of the movable mirror 76 with respect to the fixed mirror, along the axis XX', and therefore modifies the length of the resonant cavity.

The length d of the Fabry-Pérot cavity satisfies the relationship:

$$2nd = m\lambda \qquad (1)$$

where d is the length which separates the reflective surfaces, m is an integer number, n is the refractive index of the medium situated between the two mirrors and $\lambda$ is the wavelength. Any variation in d therefore brings about a variation in the central wavelength of the passband of the interferometer.

The cavity thus formed defines, from the electrical point of view, a capacitance $C_1$ between the control electrodes 80 and the floating electrode 79. In fact, the application of an electrical voltage between the control electrodes modifies, through the capacitance $C_1$ of the air gap, the potential of the floating electrode 79 and, thus, the movable mirror 76 is attracted in the direction of the fixed mirror.

The floating electrode can be implemented on the substrate 70 (it is then associated with, or implemented on, the movable mirror 76), the control electrodes being associated with the fixed mirror.

A control electrode associated with each mirror (fixed and movable) can also be implemented. Nevertheless, the implementation of a system with a floating electrode makes it possible to avoid one level of contact connections, which simplifies the device and its method of implementation.

In FIG. 2, it is the membrane 56 which carries on its surface the floating electrode (doped Si layer).

A method of implementing a device of the type already described above in relation to FIG. 2 will be described in relation to FIGS. 5A to 5K.

In a first step (FIG. 5A) a semiconductor substrate 2 (preferably of silicon) is etched, and a metallic deposit 17 is implemented at the bottom of one of the chambers obtained by etching.

Next (FIG. 5B) an $Si_3N_4$—$SiO_2$—TiN deposit 19 is implemented on the front face of a semiconductor substrate 50.

Figure 5A:
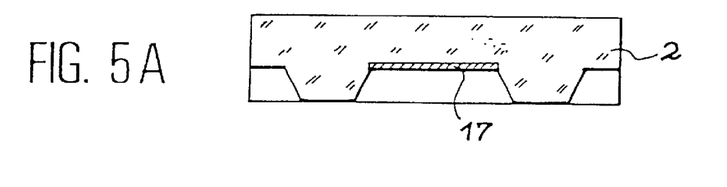
FIGS. 5A to 5K depict steps of implementing a device according to the invention.
Figure 5B:
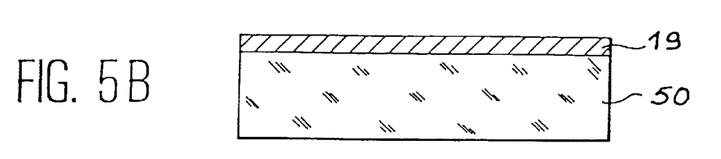
Figure 5C:
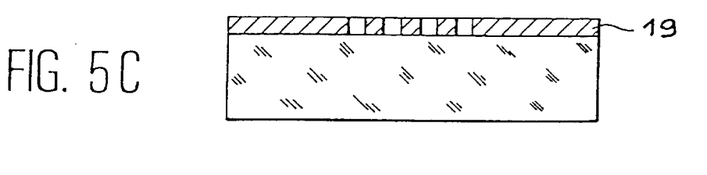
Figure 5D:
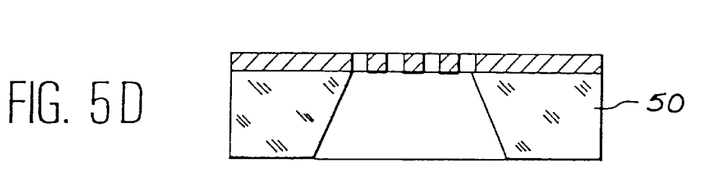
Figure 5E:
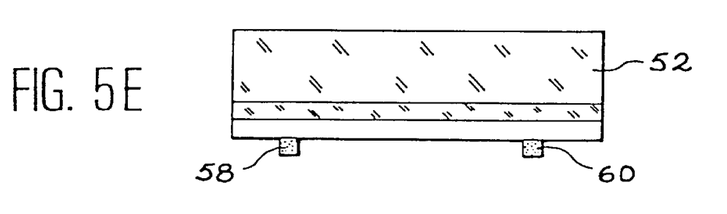
Figure 5F:
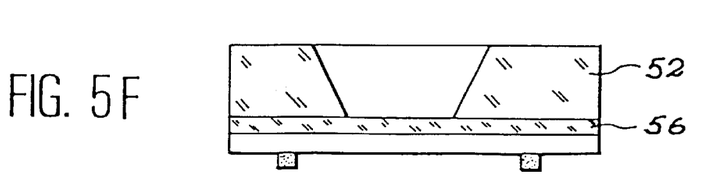

This deposit 19 is etched (FIG. 5C). Then, freeing of the membrane is implemented by the rear face of the substrate, by etching the latter (FIG. 5D).

Next (FIG. 5E) an $SiO_2$ deposit is implemented on the rear face of an "SOI" type wafer 52, and pads 58, 60 are etched in this layer. The substrate 52 is next etched so as to implement the membrane 56.

Figure 5G:
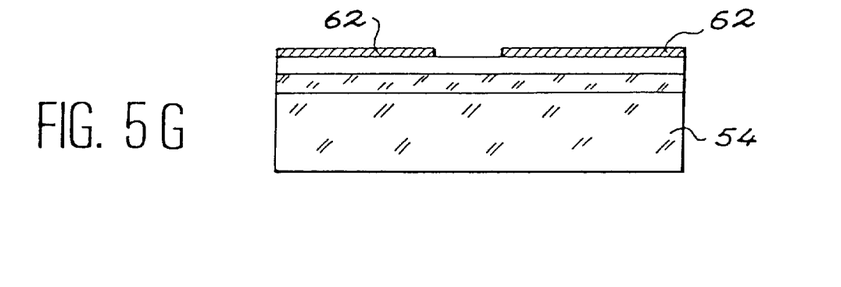
Figure 5H:
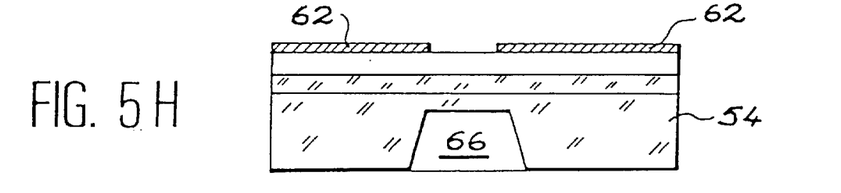

On another "SOI" type substrate 54, a metallic deposit is implemented on the front face, which is etched in order to obtain the control electrodes 62 (FIG. 5G). The substrate 54 is next etched (FIG. 5H) so as to clear the micro-trough 66.

Figure 5I:
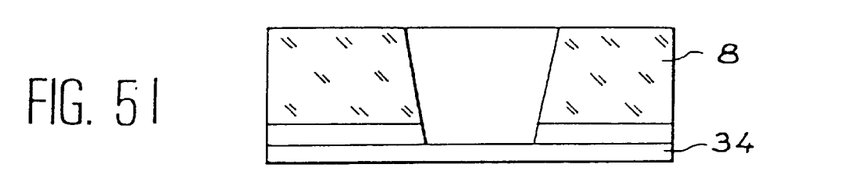
Figure 5J:
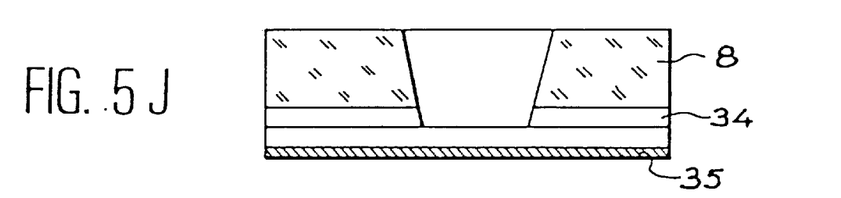

A fourth wafer 8, also of "SOI" type, is etched so as to implement the membrane 34 on the front face (FIG. 5I). A metallic deposit 35 is implemented on the front face of the substrate 8 (FIG. 5J).

Figure 5K:
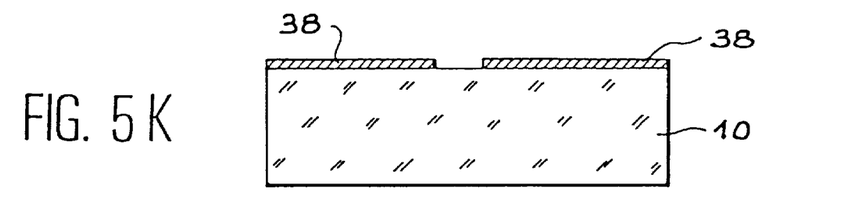

On an "SOI" type substrate 10, a metallic deposit, for example of gold, is implemented, which is next etched so as to implement the microphone electrodes 38 (FIG. 5K).

Silica pads next make it possible to adjust the different wafers with respect to one another. Resin sealings 22, 64, 66, 68, 44 next make it possible to obtain the stack illustrated in FIG. 2.

A method of implementing the devices described above in relation to FIGS. 3 and 4 will now be described in relation to FIGS. 6A to 6J.

First of all, in a first step (FIG. 6A) a first wager 2 of a semiconductor material (preferably silicon) is etched, so as to clear cavities therein. At the bottom of one of the cavities, a metallic deposit 17 is implemented.

Then (FIG. 6E) an $Si_3N_4$—$SiO_2$—TiN deposit 19 is implemented on the rear face of an "SOI" type substrate 4.

Figure 6A:
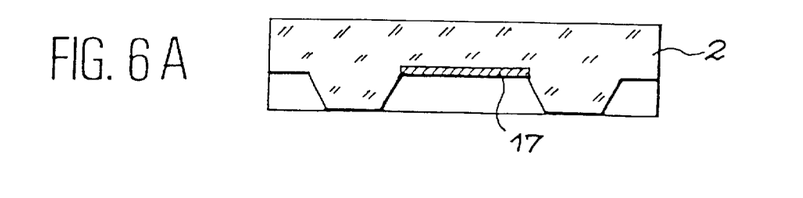
FIGS. 6A to 6J depict steps of implementing another device according to the invention.
Figure 6B:
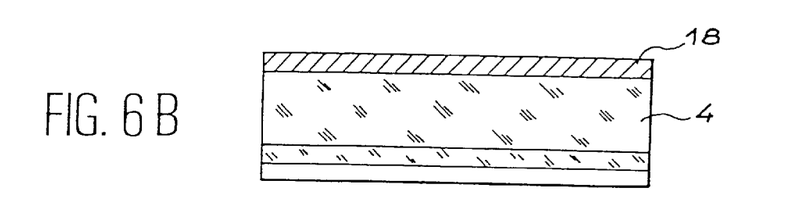
Figure 6C:
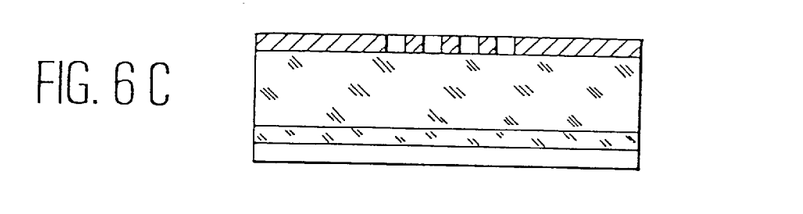

Holes are next etched in this deposit (FIG. 6C).

Figure 6D:
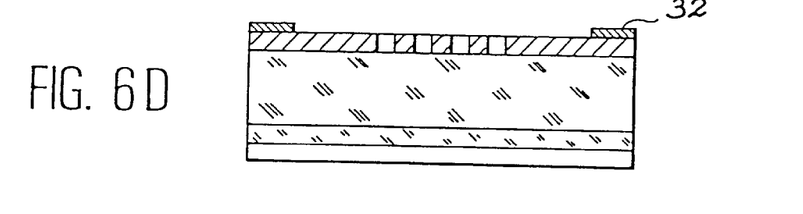

Then (FIG. 6D) an $SiO_2$ deposit is implemented and etched so as to open contact supports thereon: a gold deposit on these contact supports allows implementation of the contacts 32 (FIG. 6D).

Figure 6E:
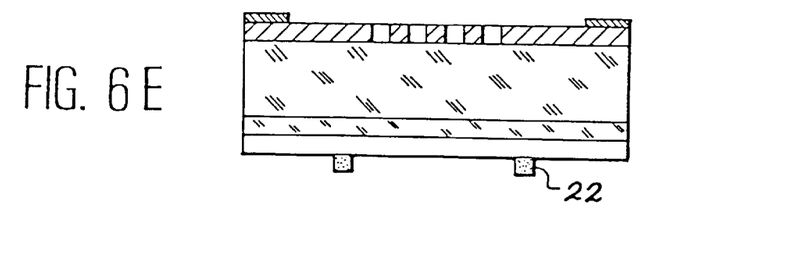
Figure 6F:
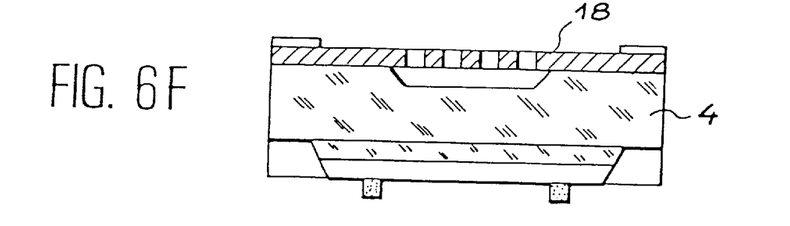
Figure 6G:
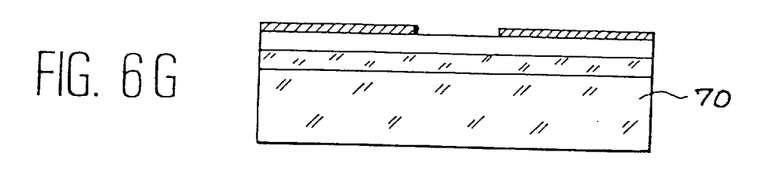
Figure 6H:
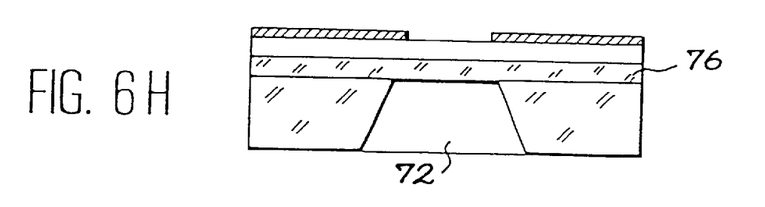

An $SiO_2$ deposit is next implemented on the front face, then etched so as to clear the pads 22 (FIG. 6E).

The membrane 18 is next freed by etching (FIG. 6F), in the area situated under the holes etched in the layer 18. Lateral cavities can also be cleared to facilitate contacts to be made on the substrate opposite.

Next (FIG. 6G) a metallic deposit 80 is implemented, then etched, on the front face of a wafer 70, of the "SOI" type. This wafer is next etched on the rear face (FIG. 6H) so as to clear the membrane 76 and form the micro-trough 72.

The device of FIG. 4 can then be implemented, by assembling the elements described above with a fourth wafer 100 of semiconductor material. The assembly is implemented in the same manner as described above (use of pads and sealing by resin seals).

Figure 6I:
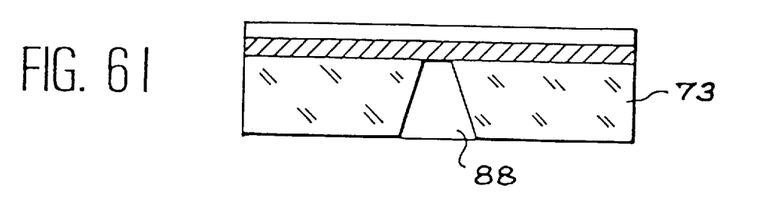
Figure 6J:
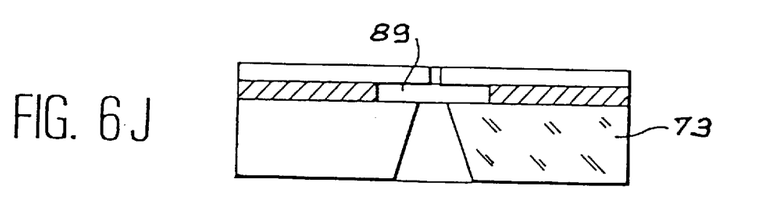

For the embodiment of FIG. 3, the method continues with the steps illustrated in FIGS. 6I and 6J.

An "SOI" type wafer 72 is etched so as to clear the rear volume 88 of the microphone, behind the membrane of the latter.

Then (FIG. 6J) a hole 89 freeing the membrane is etched, and the latter is freed by the front face of the substrate 72. Lateral etching and a metallic deposit allows implementation of the contacts 84, 86 (see FIG. 3). The assembly of this substrate with the preceding substrates is implemented in the manner already described above.

A method for implementing a device as described above in relation to FIG. 1 includes the steps for implementing and machining the wafers 2, 4 of the device of FIG. 3 (but without the implementation of the mirror 78 and the electrode 79) and steps for implementing the wafers 8, 10 of the device of FIG. 2 (implementation of the micro-trough and the microphone). It therefore suffices to select the necessary method steps from among those described above in relation to FIGS. 5A–5K and 6A–6J.

For all the embodiments described above, the substrates selected are preferably silicon substrates. Thus, the machined wafers have thicknesses of the order of a few hundred micrometres (between 100 $\mu$m and 1 mm, for example 450 or 500 $\mu$m). The superposition of 4, 5 or 6 machined wafers with the corresponding elements, in accordance with the invention, therefore leads to a device having a total thickness between 500 $\mu$m and 2 to 3 mm. The micro-trough 12 (FIGS. 1, 2), 72 (FIGS. 3, 4) typically has a section of 2 mm×2 mm, while the membrane 34 (FIGS. 1, 2), 76 (FIGS. 3, 4) has a thickness typically between 0.1 $\mu$m and a few micrometres (up to 10 $\mu$m, for example: 5 $\mu$m).

Furthermore, a substrate bonding technique has been described above; pads are used to control the air thickness between two substrates, while the sealings are carried out with the help of resin at high temperature (200° C.). Other substrate assembly techniques, derived from microelectronics, can also be used. For example, the so-called "Anodic Bonding" technique (sealing of silicon on glass and under an electric field at 400° C.) allows implementation of a device according to the invention.

Use can also be made of the so-called SDB ("silicon direct bonding") technique (sealing of oxide on oxide at high temperature (>800° C.)) or the eutectic soldering technique described in "sensors and actuators", A45 (p. 227–236).

What is claimed is:

1. A photoacoustic spectrometer having:
   an infrared source implemented in a first semiconductor substrate,
   a filter implemented with the help of a second semiconductor substrate,
   a micro-trough formed in a third semiconductor substrate,
   a microphone implemented with the help of the third semiconductor substrate and a fourth semiconductor substrate.

2. A photoacoustic spectrometer, having:
   an infrared source implemented in a first semiconductor substrate,
   a Fabry-Pérot interferential filter formed with the help of a second and a third semiconductor substrate,
   a micro-trough implemented partially in the third semiconductor substrate and partially in a fourth semiconductor substrate,
   a microphone implemented with the help of the fourth and a fifth semiconductor substrate.

3. A photoacoustic spectrometer, having:
   an infrared source, implemented in a first semiconductor substrate,
   a Fabry-Pérot interferential filter formed with the help of the first and a second semiconductor substrate,
   a micro-trough implemented in the second semiconductor substrate,
   a microphone implemented on the surface of a third semiconductor substrate.

4. A photoacoustic spectrometer, having:
   an infrared source implemented in a first semiconductor substrate,
   a Fabry-Pérot interferential filter implemented with the help of the first and a second semiconductor substrates,
   a microphone and a micro-trough, implemented in the second semiconductor substrate.

5. A spectrometer according to claim 1, the infrared source being placed in a cavity under vacuum.

6. A spectrometer according to claims 1, an etched substrate closing the infrared source, a reflecting element being disposed in a cavity etched in this substrate.

7. A spectrometer according to claim 1, the interferential filter being a filtering substrate.

8. A spectrometer according to claim 1, one of the walls of the micro-trough being constituted by the microphone membrane.

9. A spectrometer according to claim 1, the microphone having a membrane, a first electrode associated with this membrane, and a second electrode, the excess pressures n in the micro-trough being detected by variation in the capacitance of the air gap between the first and second electrodes.

10. A method of implementing a photoacoustic spectrometer, in particular according to claim 1, including:
    the implementation of an infrared source in a first semiconductor substrate,
    the implementation of an interferential filter with the help of a second semiconductor substrate,
    the implementation of a micro-trough in a third semiconductor substrate,
    the implementation of a microphone with the help of the third and a fourth semiconductor substrates,
    the assembly of the infrared source, the filter, the micro-trough and the microphone by assembly of the substrates.

11. A method of implementing a photoacoustic spectrometer, in particular according to claim 2, including:
    the implementation of an infrared source in a first semiconductor substrate,
    the implementation of a tunable interferential filter with the help of a second and a third semiconductor substrates,
    the implementation of a micro-trough, partially in the third semiconductor substrate and in a fourth semiconductor substrate,
    the implementation of a microphone with the help of the fourth and a fifth semiconductor substrates.

12. A method of implementing a photoacoustic spectrometer, in particular according to claim 3, including:
    the implementation of an infrared source in a first semiconductor substrate,
    the implementation of a filter with the help of the first and a second semiconductor substrates,
    the implementation of a micro-trough, in the second semiconductor substrate,
    the implementation of a microphone, on the surface of a third semiconductor substrates, the assembly of the infrared source, the filter, the micro-trough and the microphone by assembly of the substrates.

13. A method of implementing a photoacoustic spectrometer, in particular according to claim 4, including:
the implementation of an infrared source in a first semiconductor substrate,
the implementation of an interferential filter and a microphone with the help of the first and a second semiconductor substrates,
the implementation of a micro-trough in the second semiconductor substrate,
the assembly of the infrared source, the filter, and the microphone and the micro-trough by assembly of the first and second substrates.

14. A method according to claim 12, the microphone being implemented by etching of the third substrate in order to clear a conductive membrane, and formation of a counter electrode.

15. A method according to one of claims 10 to 13, the assembly being implemented by "Anodic bonding" or by sealing of the substrates.

16. A method according to claim 15, the assembly being implemented by resin sealing.

17. A method according to one of claims 11 to 13, the filter being a Fabry-Pérot interferential filter, its implementation bringing into play:
the implementation of a first mirror and a first associated control electrode,
the implementation of a second mirror and a second associated control electrode, one out of the first and second mirrors being fixed and the other being movable.

18. A method according to either of claim 17, the movable mirror being implemented by etching of one of the substrates, the etched volume defining the micro-trough.

19. A method according to one of claims 11 to 13, the filter being a Fabry-Pérot interferential filter, its implementation bringing into play:
the implementation of a first mirror and a floating electrode,
the implementation of a second mirror and associated control electrodes, one out of the first and second mirrors being fixed and the other being movable.

20. A method according to one of claims 10 to 13, the micro-trough being implemented by etching of at least one semiconductor substrate until a membrane is obtained, the microphone next being implemented by formation of an electrode on the membrane and formation of electrodes on another substrate.

21. A spectrometer according to one of claims 1 to 4, the infrared source being able to be modulated electrically.

22. A spectrometer according to claim 21, the infrared source having a metallic grid or filament supported by a membrane above a cavity etched in the first semiconductor substrate.

23. A spectrometer according to one of claims 1 to 4, the infrared source having a metallic grid or filament supported by a membrane above a cavity etched in the first semiconductor substrate.

24. A spectrometer according to claim 23, the metallic grid or filament being made of silicon nitride, or platinum, or tantalum, or titanium, or tungsten, or molybdenum, or chromium, or nickel, or one of their alloys.

25. A spectrometer according to one of claims 2 to 4, the interferential filter being a Fabry-Pérot tunable filter.

26. A spectrometer according to claim 25, the interferential filter having a first, fixed, mirror and a second, movable, mirror, these mirrors delimiting, at rest, a resonant cavity of length d, and first and second control electrodes respectively associated with these first and second mirrors, the application of an electrical voltage between the control electrodes allowing implementation of a displacement of the movable mirror with respect to the fixed mirror, and therefore modifying the length d of the resonant cavity.

27. A spectrometer according to claim 26, the movable mirror being implemented by a membrane situated above a cavity implemented in the second semiconductor substrate.

28. A spectrometer according to claim 26, the movable mirror being composed of a membrane etched in the second semiconductor substrate.

29. A spectrometer according to claim 26, the mirrors of the filter being implemented by stacking of multilayers at $\lambda/4$, on the surface of the first and second or second and third semiconductor substrates.

30. A spectrometer according to claim 26, the control electrodes forming an input diaphragm of the micro-trough.

31. A spectrometer according to claim 26, the membrane of the tunable filter also constituting the movable mirror of the tunable filter.

32. A spectrometer according to claim 25, the Fabry-Pérot tunable filter having:
a first mirror, with which a floating electrode is associated,
a second mirror, with which a first and a second control electrode are associated, one out of the first and second mirrors being provided fixed and the other movable,
a resonant cavity, of length d, delimited by the first and second mirrors, the application of an electrical voltage between the two control electrodes bringing about a displacement of he movable mirror with respect to the fixed mirror and therefore modifying the length d of the resonant cavity.

33. A spectrometer according to claim 32, the control electrodes being formed on either side of a movable reflective area of the second mirror.

34. A spectrometer according to claim 33, the movable reflective area having a circular form.

35. A spectrometer according to claim 32, the movable mirror being implemented by a membrane situated above a cavity implemented in the second semiconductor substrate.

36. A spectrometer according to claim 32, the movable mirror being composed of a membrane etched in the second semiconductor substrate.

37. A spectrometer according to claim 32, the mirrors of the filter being implemented by stacking of multilayers at $\lambda/4$, on the surface of the first and second or second and third semiconductor substrates.

38. A spectrometer according to claim 32, the control electrodes forming an input diaphragm of the micro-trough.

39. A spectrometer according to claim 32, the membrane of the tunable filter also constituting the movable mirror of the tunable filter.

40. A spectrometer according to either of claims 1 or 2, the microphone having a membrane and a first electrode associated with this membrane, both implemented on the third or the fourth semiconductor substrate, and a second electrode, implemented on the fourth or the fifth semiconductor substrate.

41. A spectrometer according to claim 3 or 4, the microphone membrane being implemented in a doped semiconductor material, the microphone also having a counter electrode.

42. A spectrometer according to claim 41, the microphone membrane being situated on the surface of the third or the fourth substrate, the latter being etched under the membrane.

* * * * *